United States Patent
Jacobsen et al.

(10) Patent No.: US 7,666,158 B2
(45) Date of Patent: Feb. 23, 2010

(54) METHODS AND DEVICES FOR REDUCING A FOOT DROP CONDITION

(76) Inventors: Cynthia Jacobsen, 938 Tyree Springs, White House, TN (US) 37188; Jay Ellis, 119 Circle Dr., Cottontown, TN (US) 37048

( * ) Notice: Subject to any disclaimer, the term of this patent is extended or adjusted under 35 U.S.C. 154(b) by 0 days.

(21) Appl. No.: 11/971,950

(22) Filed: Jan. 10, 2008

(65) Prior Publication Data
US 2008/0171956 A1    Jul. 17, 2008

Related U.S. Application Data

(60) Provisional application No. 60/880,253, filed on Jan. 12, 2007.

(51) Int. Cl.
A61F 5/00      (2006.01)
A43C 11/00    (2006.01)
A43B 23/00    (2006.01)
A43B 5/00     (2006.01)

(52) U.S. Cl. .............. 602/28; 602/23; 602/29; 602/5; 602/1; 602/30; 36/50.1; 36/136; 36/83; 36/45

(58) Field of Classification Search ............ 602/28, 602/5, 1, 23, 29, 30, 24; 36/50.1, 136, 83, 36/45
See application file for complete search history.

(56) References Cited
U.S. PATENT DOCUMENTS

| | | | |
|---|---|---|---|
| 2,584,010 A * | 1/1952 | Goffredo .............. 602/28 |
| 3,504,668 A * | 4/1970 | Boudon ............... 602/28 |
| 3,986,501 A | 10/1976 | Schad | |
| 4,289,122 A | 9/1981 | Mason et al. | |
| 4,566,447 A | 1/1986 | Deis | |
| 4,651,733 A | 3/1987 | Mobin-Uddin | |
| 4,817,589 A | 4/1989 | Wertz | |
| 5,092,319 A * | 3/1992 | Grim .................. 602/27 |
| 5,382,224 A | 1/1995 | Spangler | |
| 5,897,515 A | 4/1999 | Willner et al. | |
| 6,409,692 B1 | 6/2002 | Covey | |
| 6,602,217 B2 | 8/2003 | Crawford et al. | |
| 6,793,640 B1 | 9/2004 | Avon | |
| 6,926,687 B2 * | 8/2005 | Shields ................ 602/24 |
| 7,458,950 B1 * | 12/2008 | Ivany .................. 602/28 |
| 2005/0126047 A1 | 6/2005 | Kruijsen | |
| 2005/0177083 A1 | 8/2005 | Heil | |
| 2007/0100268 A1 | 5/2007 | Fisher | |

FOREIGN PATENT DOCUMENTS

WO    WO 2005/030088    4/2005

* cited by examiner

*Primary Examiner*—Patricia M Bianco
*Assistant Examiner*—Tarla R Patel

(57) ABSTRACT

Embodiments are provided to reduce a foot drop condition. In an embodiment, an adjustable apparatus includes a lower leg member that can be secured to a lower leg portion of a user. The lower leg member can be adjustably and releasably coupled to a user's footwear to assist in orienting the user's foot at a desired orientation. In one embodiment, an apparatus includes a molded brace member that can be secured to a user's lower leg below the calf. The molded brace member can be sized and dimensioned to correspond to the associated measurements of the lower leg of a user afflicted with a foot drop condition. A lacing member can be coupled to the user's footwear and coupled to the molded brace member to orient the user's foot at a desired orientation.

20 Claims, 14 Drawing Sheets

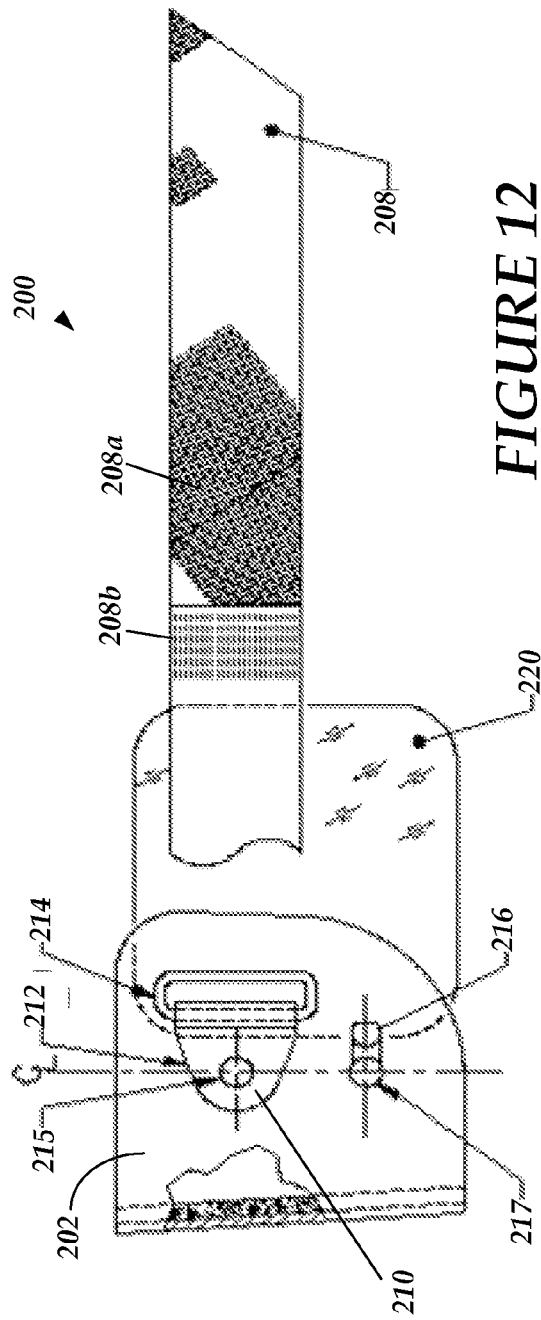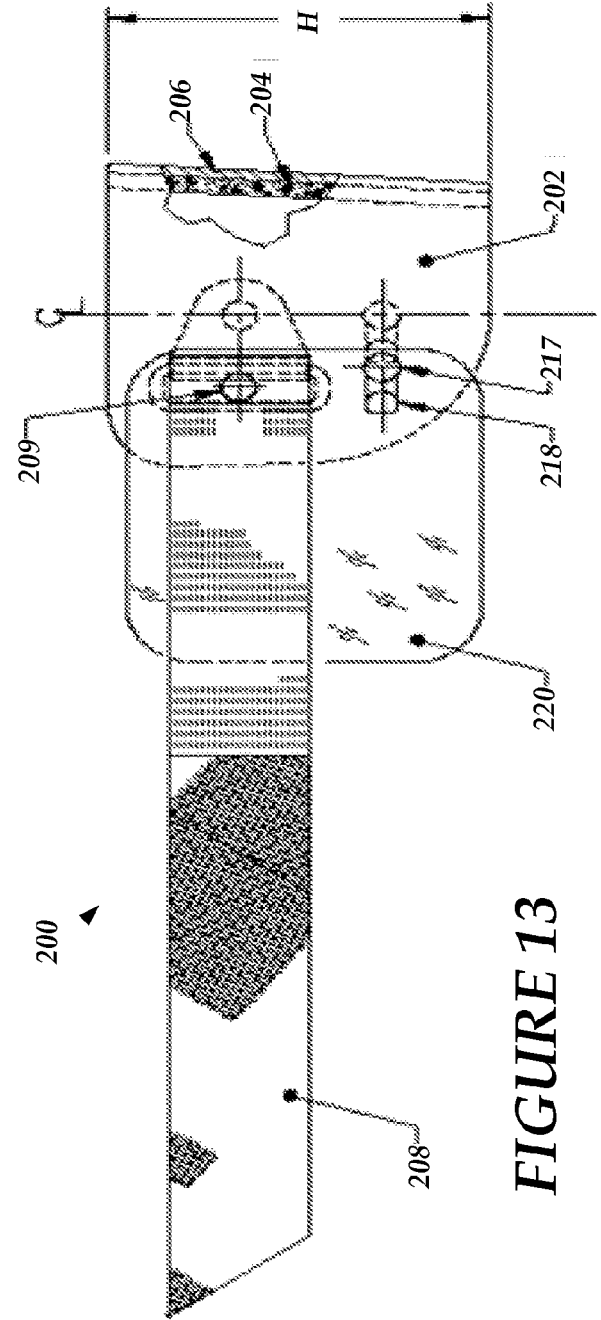
FIGURE 12
FIGURE 13

METHODS AND DEVICES FOR REDUCING A FOOT DROP CONDITION

RELATED APPLICATIONS

This application claims priority to U.S. Provisional Patent Application No. 60/880,253, filed Jan. 12, 2007.

BACKGROUND

The condition of "foot drop" can significantly affect an individual's quality of life. An individual having a foot drop condition may have self-esteem issues, a lack of confidence when being active, and other associated psychological, physical, and personal issues associated with the condition. Muscular, skeletal, and/or neurological issues can be associated with and can also contribute to a foot drop condition. For example, weakened dorsiflexor and other muscles can affect an individual's ability to clear the foot during a swing phase for a heel strike. A foot drop condition can result in an individual's reduced ability to rotate the foot and toes of an affected leg upward while walking or running.

An individual afflicted with a foot drop condition may be seen to drag their toes of the affected foot, which can result in tripping or loss of balance, since the user is unable or has limited ability to pull the toes upward and away from the ground. A foot drop condition can occur as a result of an injury, neuromuscular disease, stroke, diabetes, and other ailments. Individuals afflicted with a foot drop condition can be seen trying to walk with an exaggerated flexion of the hip, thigh, and/or knee to prevent the toes from catching on the ground or some other object. In some cases, a foot drop condition can require one or more surgical procedures (e.g. triple arthidosis, etc.) which still may not resolve the associated issues. Medical devices and systems have also been created in attempts to reduce or alleviate a foot drop condition.

SUMMARY

This summary is provided to introduce a selection of concepts in a simplified form that are further described below in the Detailed Description. This summary is not intended to identify key features or essential features of the claimed subject matter, nor is it intended as an aid in determining the scope of the claimed subject matter.

Embodiments are provided to reduce a foot drop condition, but the embodiments are not so limited. In an embodiment, an adjustable apparatus includes a lower leg member that can be secured to a lower leg portion of a user. The lower leg member can be adjustably and releasably coupled to a user's footwear to assist in orienting the user's foot at a desired orientation. In one embodiment, an apparatus includes a molded brace member that can be secured to a user's lower leg below the calf and above the foot. The molded brace member can be sized and dimensioned to correspond to the associated measurements of the lower leg of a user afflicted with a foot drop condition. A lacing member can be coupled to the user's footwear and coupled to the molded brace member to orient the user's foot at a desired orientation.

These and other features and advantages will be apparent from a reading of the following detailed description and a review of the associated drawings. It is to be understood that both the foregoing general description and the following detailed description are explanatory only and are not restrictive of the invention as claimed.

BRIEF DESCRIPTION OF THE DRAWINGS

FIG. 12 is a right side view of an apparatus that can be used to reduce a foot drop condition under an embodiment.
FIG. 13 is a left side view of the apparatus of FIG. 12.

DETAILED DESCRIPTION

Figure 1:
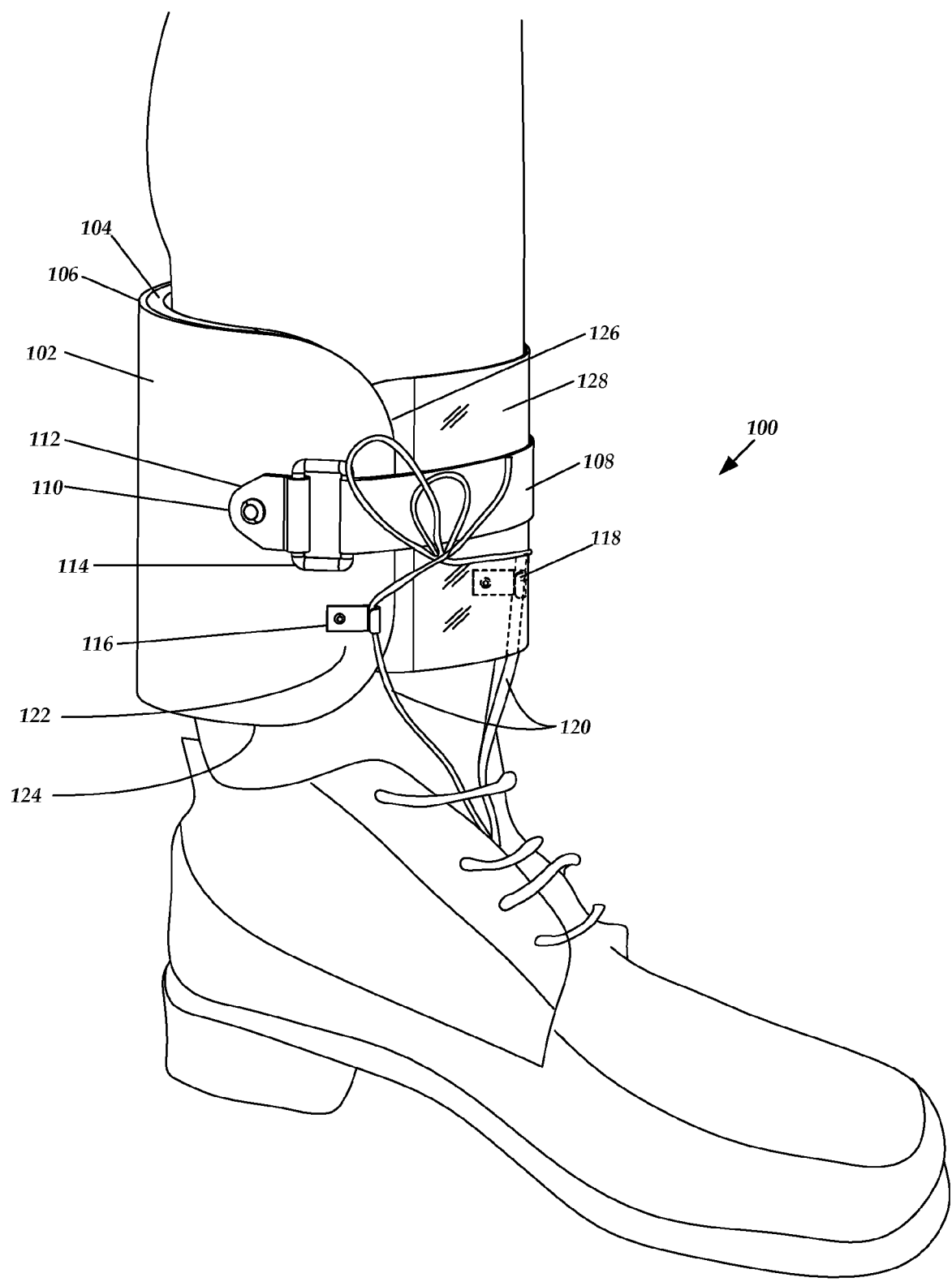
FIG. 1 illustrates an apparatus that can be used to reduce a foot drop condition under an embodiment.

Embodiments are provided to reduce a foot drop condition. Various embodiments provide an apparatus, method of using the apparatus, method of making the apparatus and other features that assist in reducing a foot drop condition and other associated conditions. In an embodiment, an adjustable apparatus includes a lower leg member that can be secured to a lower leg portion above the ankle and below the calf muscle. The apparatus can be adjustably coupled to a user's footwear to orient the user's foot at a desired orientation with respect to the lower leg. In one embodiment, an apparatus includes a molded brace member that can be secured to a user's lower leg below the calf. The molded brace member can be sized and dimensioned to correspond to the associated measurements of the lower leg of the user afflicted with a foot drop condition.

A lacing member or other coupling can be coupled to the user's footwear and adjustably and releasably coupled to the molded brace member. For example, a shoelace, string, rope, or similar cordage can be threaded through shoe eyelets or retainers and under existing laces of the footwear before being coupled to attachment members of the molded brace member to secure the foot at a desired orientation with respect to the molded brace member. In one embodiment, footwear, such as dress shoes or boots for example, can be modified such that a lacing member can be threaded from near the forward footwear portion and below a dorsal portion or upper shoe surface. Thereafter, the modified footwear can be adjustable and releasably coupled to the molded brace member using the lacing member and attachment members to orient the user's foot to a desired orientation (e.g., as measured by the angle between the shin and dorsal portion of the foot). The apparatus can be configured as an effective, comfortable, and discreet orthosis device to reduce a foot drop condition.

The lower leg member can serve as an anchor to allow an affected foot to be lifted to a level that is comfortable for a user. For example, the lift can be provided using durable shoe strings that are laced in the eyelets of the user's existing footwear and the laces can be attached to a location or locations on the lower leg member. Once the foot has been lifted to a desired orientation (e.g. rotational angle), the durable shoe laces can be secured (e.g. tied, cord lock, cord stop, cord fastener, etc.), thereby securing and orienting the lifted foot. The durable shoe laces can be adjusted to decrease or increase an amount of lift orientation. A tongue member and/or an inner liner or layer can be configured to provide added cushioning, moisture dissipation, and/or breathability.

As described below, embodiments are described to provide a comfortable, effective, and discreet solution for those afflicted with a foot drop condition. For example, a user can continue to wear normal outfits and footwear while using an apparatus according to an embodiment, since the apparatus is not bulky or cumbersome and is not required to be inserted in the footwear. The embodiments provide effective solutions to reduce a foot drop condition for individuals with injuries, neuromuscular diseases, strokes, diabetes, and other conditions.

In the following description, numerous specific details are introduced to provide a thorough understanding of, and enabling description for, embodiments of the invention. One skilled in the relevant art, however, will recognize that the invention can be practiced without one or more of the specific details, or with other components, etc. In other instances, well-known structures or operations are not shown, or are not described in detail, to avoid obscuring aspects of the invention.

Referring now to the drawings, in which like numerals represent like elements, various aspects of the present invention will be described.

FIG. 1 illustrates an apparatus 100 that can be used to reduce a foot drop condition, under an embodiment. The apparatus 100 (also referred to as a dorsal foot orthosis (DFO)) can be used by a user to improve mobility issues and conditions, including issues associated with walking, standing, running, etc. For example, the apparatus 100 can be used by a user to reduce the likelihood of tripping due to an unintentional drop of the foot. The apparatus 100 can be readily manufactured and tailored to a size and a dimension of a specific user. For example, the apparatus 100 can be molded to a size and dimension that conforms to a user's lower leg by measuring the circumference of the user's lower leg above the ankle and forming a mold based on the circumference measurement that can be used to manufacture the apparatus 100.

As shown in FIG. 1, the apparatus 100 is shown as worn by a user after being adjusted to a desired orientation to lift the dorsal area of the foot towards the lower leg. The apparatus 100 can be adjusted to a desired orientation according to a user's preference. The apparatus 100 includes a lower leg member 102 (sometimes referred to as a cuff member or brace member). The lower leg member 102 includes an inner layer 104 and an outer layer 106. In one embodiment, the lower leg member 102 can be molded using a vacuum molding process to have a height of about 2 inches to about 6 inches, wherein the inner layer 104 includes a breathable cushioning material having a thickness of about 0.125 inches to about 0.50 and the outer layer 106 includes a sturdy, flexible, and lightweight material having a thickness of about 0.0625 inches to about 0.25 inches. The lower leg member 102 can be manufactured to encompass a substantial portion (e.g., greater than sixty percent of a measured lower leg circumference) of the lower leg circumference of an individual afflicted with a foot drop condition.

In an embodiment, the inner layer 104 comprises a cushioning material, such as a heat moldable foam material for example, and the outer layer 106 comprises a rigid but flexible material, such as a thermoplastic or other plastic material for example. In one embodiment, the lower leg member 102 can be molded into a frustoconical shape having a substantially C-shaped cross-section (see FIGS. 14 and 15) that conforms to a size and dimension of a user afflicted with a foot drop condition. However, the size, dimension, configuration, and materials of the lower leg member 102 can be configured to conform to a particular user and any associated requirements.

The apparatus 100 also includes an elongate closure member 108 that can be attached to the lower leg member 102 and used to secure the lower leg member 102 to user's leg above the ankle and below the calf muscle. In one embodiment, the elongate closure member 108 comprises a strap having a length and a width that includes a first hook portion and a second loop portion. The elongate closure member 108 can be pulled tight and the first hook portion can be attached to the second loop portion to secure the lower leg member 102 to the user's lower leg. In another embodiment, the elongate closure member 108 comprises a two-piece adjustable strap member that includes male and female buckling members, snaps, or other fasteners that can be used to secure the lower leg member 102 to the user's lower leg.

Figure 2:
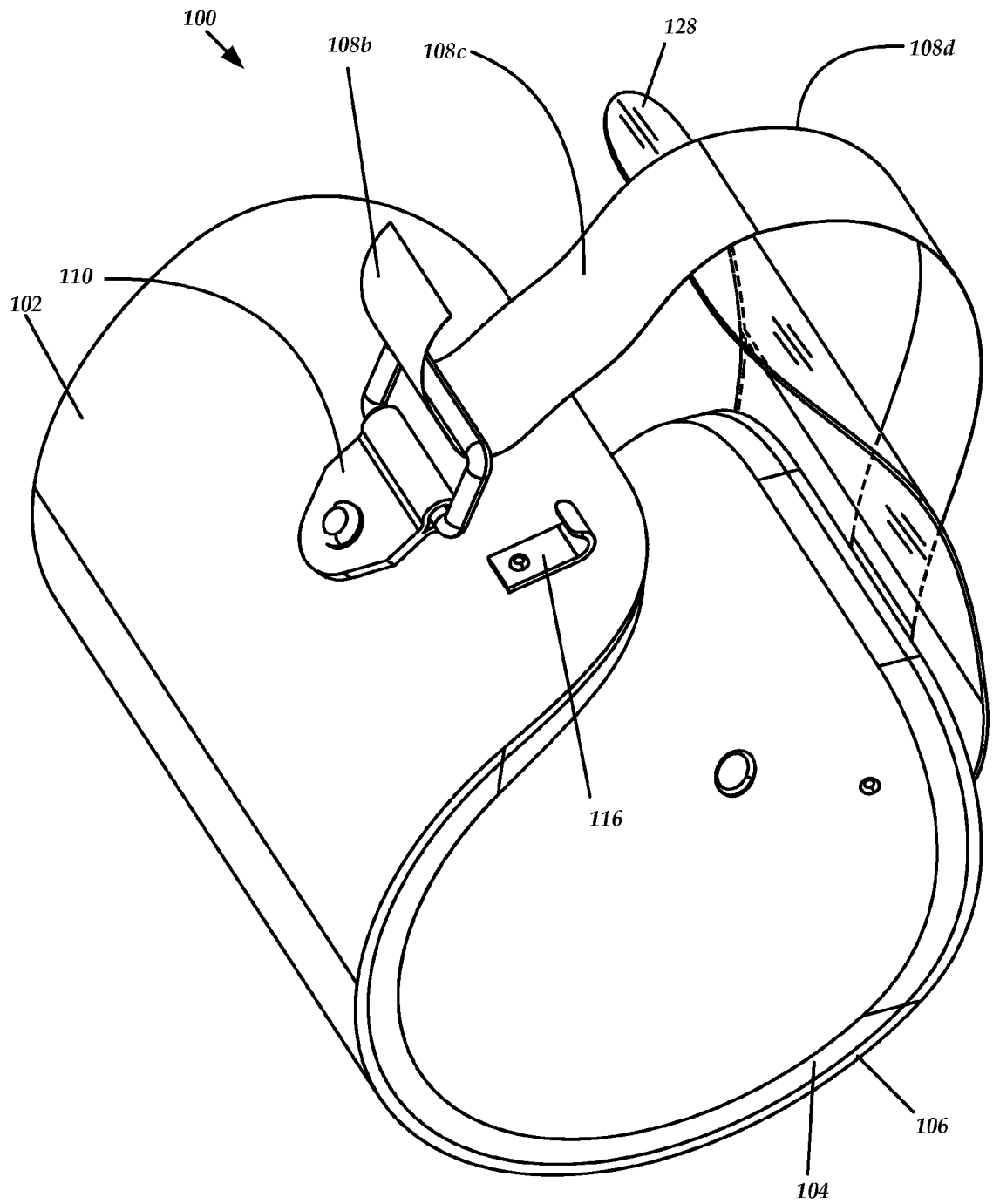
FIG. 2 is a perspective view of the apparatus of FIG. 1.
Figure 4:
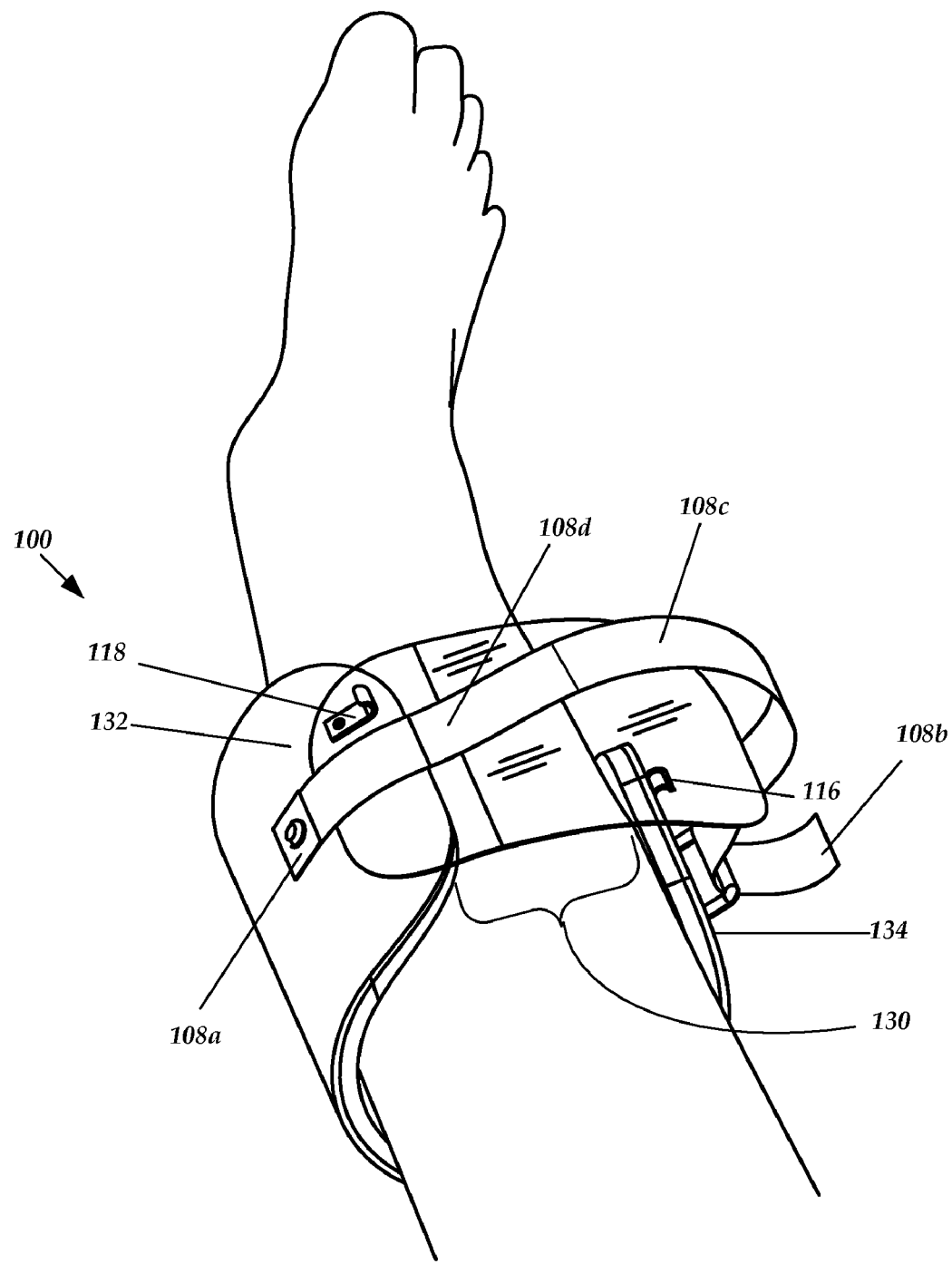
FIG. 4 depicts the apparatus of FIG. 1 coupled to a lower leg portion of a user.

As shown in FIG. 4, one end 108a of the elongate closure member 108 can be securely attached to a side portion of the lower leg member 102 and the other end 108b can be used to releasably secure the lower leg member 102 to the user's lower leg. For example, a rivet, screw, or other fastening device can be used to secure the end 108a of the elongate closure member 108 to the lower leg member 102 and the other end 108b can be releasably attached to another portion of the elongate closure member 108 or the lower leg member 102. As shown in FIGS. 2 and 4, in one embodiment, the elongate closure member 108 includes a first strap portion 108c of loop members that can be releasably attached or stuck to a second strap portion 108d of hook members.

As shown in FIG. 1, the elongate closure member 108 can be threaded through a threading member 110 and adjustably secured to compress and secure the lower leg member 102 to the user's lower leg. The threading member 110 can be used in conjunction with the elongate closure member 108 to secure the lower leg member 102 to the user's lower leg. In one embodiment, the threading member 110 includes a chafe tab portion 112 and a loop, ring, or other threading portion 114 (e.g., D-loop, D-ring, tri-ring, etc.). The threading member 110 can be securely affixed to the lower leg member 102, such as by using a rivet, screw, or other fastener for example.

The lower leg member 102 also includes a pair of attachment members 116 and 118 that can be used to couple the lower leg member 102 to a user's footwear, such as a shoe or a boot for example. For example, the pair of attachment members 116 and 118 can comprise a pair of metallic or plastic hooks, loops, rings, or other coupling structures that can be riveted or otherwise affixed to the lower leg member 102. An attachment means 120, such as a durable lace member of an elongate length of substantially non-elastic material that is used for tying or coupling for example, can be releasably and adjustably coupled to the lower leg member 102 using the pair of attachment members 116 and 118. The attachment means 120 can be implemented so as not to substantially stretch or deform and provide a substantially non-elastic securing means in order to maintain the user's foot in a desired orientation when secured.

As shown in FIG. 1, the pair of attachment members 116 and 118 can be located below the elongate closure member 108 and affixed to a lower frontal portion 122 of the lower leg member 102. In one embodiment, the pair of attachment members 116 and 118 can be located a percentage of a distance of the overall height of the lower leg member 102 as measured from a lower edge 124 and from a leading edge 126 of the lower leg member 102 (e.g., see the location of the pair of attachment members 216 and 218 of FIGS. 12 and 13).

Correspondingly, the amount and orientation of a force required to lift the affected foot can be optimized by locating the pair of attachment members 116 and 118 at the lower frontal portion 122 (in front of the ankle bone towards the user's toes) of the lower leg member 102. For example, the amount of force required to lift and maintain the foot at the desired orientation can be focused on the dorsal portion of the foot by locating the pair of attachment members 116 and 118 in the proximity of the lower frontal portion 122 of the lower leg member and securing the attachment means 120 from the footwear to the pair of attachment members 116 and 118. Moreover, the length of the attachment means 120 required to secure the foot can also be minimized by minimizing the distance between the pair of attachment members 116 and 118 and the user's footwear.

A user can pull up on the attachment means 120 (see arrows of FIG. 10) to orient the affected foot at a desirable orientation with respect to the lower leg member 102 and use the pair of attachment members 116 and 118 to support the force required to maintain the affected foot at the desired orientation. The user can use other means to assist in flexing the affected foot to a desired orientation when securing the attachment means 120 using the pair of attachment members 116 and 118. For example, the user can use a floor surface to flex the affected foot while standing and secure the apparatus 100 to orient the foot so that the toes are pulled away from the ground so as not to catch when walking or running.

As further example, a user can put the ball of the affected foot on a step, curb, chair, or other raised surface and use the user's body weight to flex the affected foot. A user can also have another person push the foot upward to obtain the desired orientation of the affected foot when securing the attachment means 120. Once the foot has been oriented to the desired orientation, the attachment means 120 can be releasably secured to maintain the affected foot at the desired orientation.

In one embodiment, an extra lace or other cordage can be included with the apparatus 100 and used to secure and maintain the affected foot at the desired orientation. The extra lace or other cordage can be coupled to the user's footwear and releasably secured to the lower leg member 102 using the pair of attachment members 116 and 118. For example, the ends of the attachment means 120 can be tied or a slidable locking member or other securing mechanism can be used to releasably secure an extra durable lace to maintain the force required to orient the foot at the desired orientation. In an alternative embodiment, shoe or boot laces already included as part of a user's footwear can be secured to the lower leg member 102 using the pair of attachment members 116 and 118.

With continuing reference to FIG. 1, the apparatus 100 also includes a tongue member 128. The tongue member 128 can be coupled to the lower leg member 102 and used to provide a shield to the elongate closure member 108 and a secured attachment means 120. The tongue member 128 can be made of plastic or another lightweight material to prevent chafing or other discomfort that may be caused by the elongate closure member 108 or a secured attachment means 120.

Figure 3:
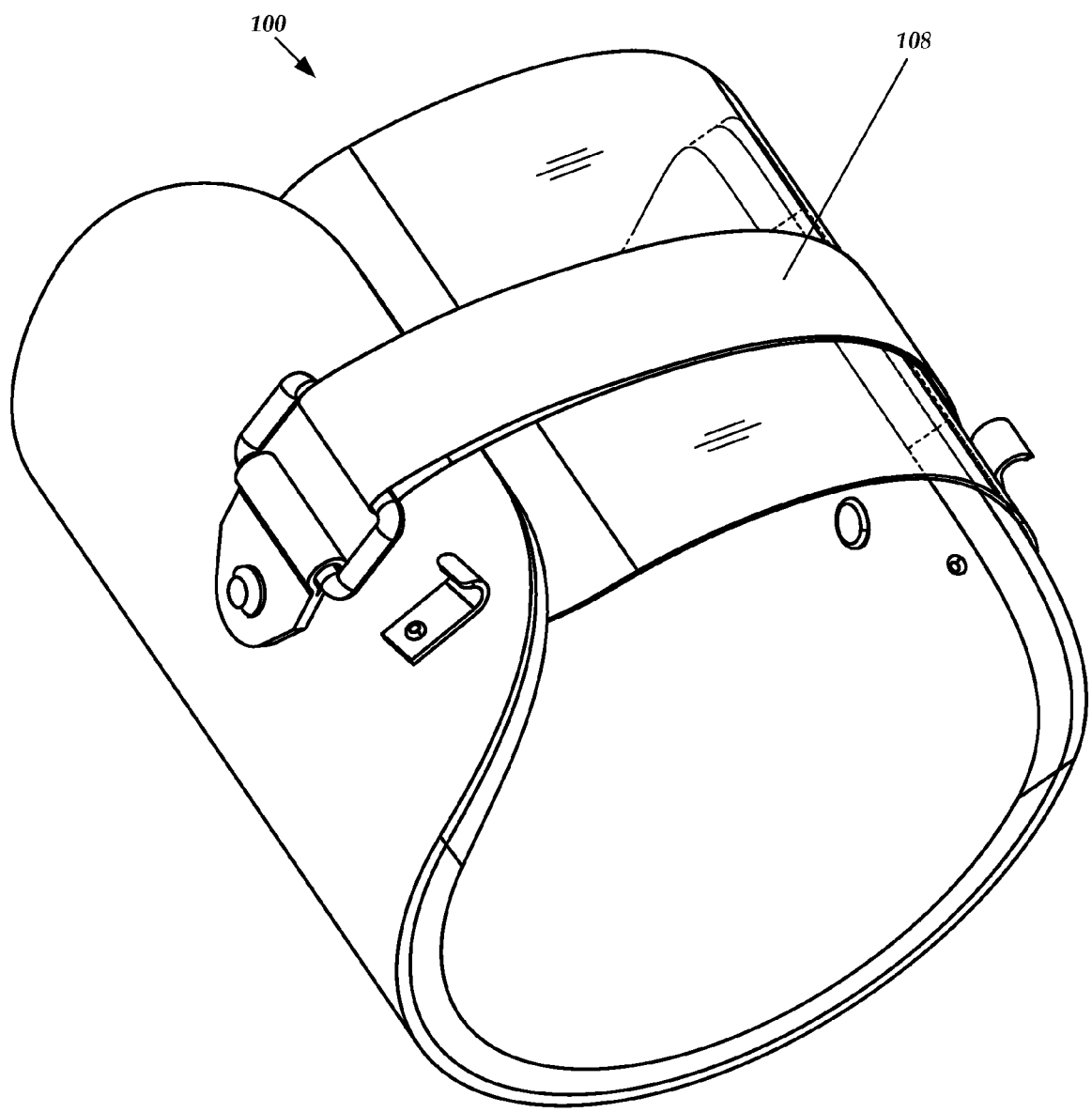
FIG. 3 is a perspective view of the apparatus of FIG. 1.

FIG. 3 is a perspective view of the apparatus 100 of FIG. 1, wherein the elongate closure member 108 is shown in a secured orientation.

FIG. 4 depicts the apparatus 100 of FIG. 1 coupled to a lower leg portion of a user. As shown in FIG. 4, the user has coupled the lower leg member 102 to a lower leg portion (e.g., above the ankle and below the calf muscle) by using the opening 130 to place the lower leg member 102 on the lower leg portion. In one embodiment, the opening 130 between opposing edges of the lower leg member 102 is about 0.50 inches to about 4 inches wide. However, the size and dimension of the opening 130 can be customized for the particular user. As shown in FIG. 4, the pair of attachment members 116 and 118 can be located on opposing sides 132 and 134 of the opening 130.

Figure 5:
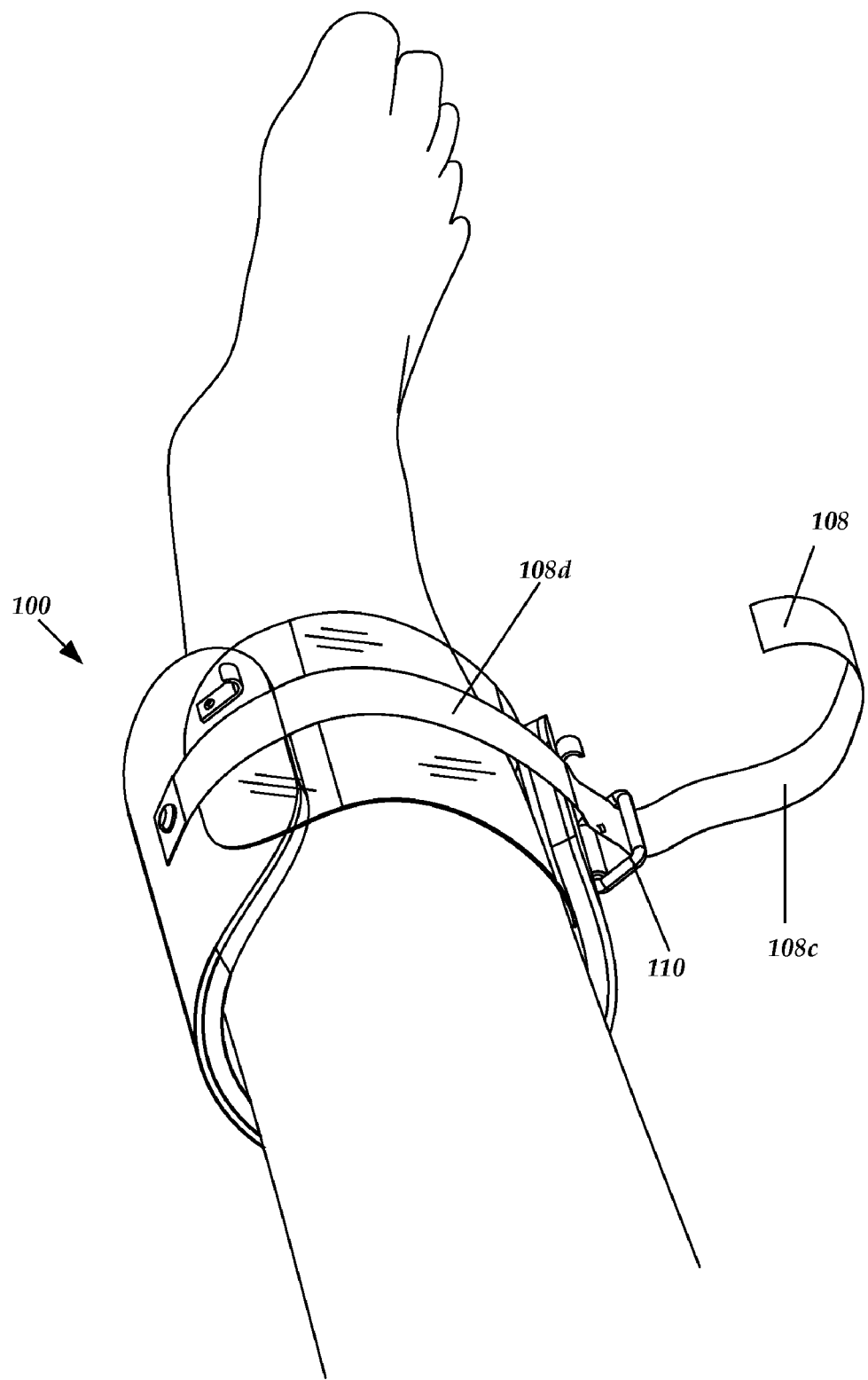
FIG. 5 depicts the apparatus of FIG. 1 coupled to the lower leg portion of the user.

FIG. 5 depicts the apparatus 100 of FIG. 1 coupled to a lower leg portion of a user. As shown in FIG. 5, the elongate closure member 108 has been threaded through the threading member 110 and tightened in preparing to secure the first portion 108*c* to the second portion 108*d*.

Figure 6:
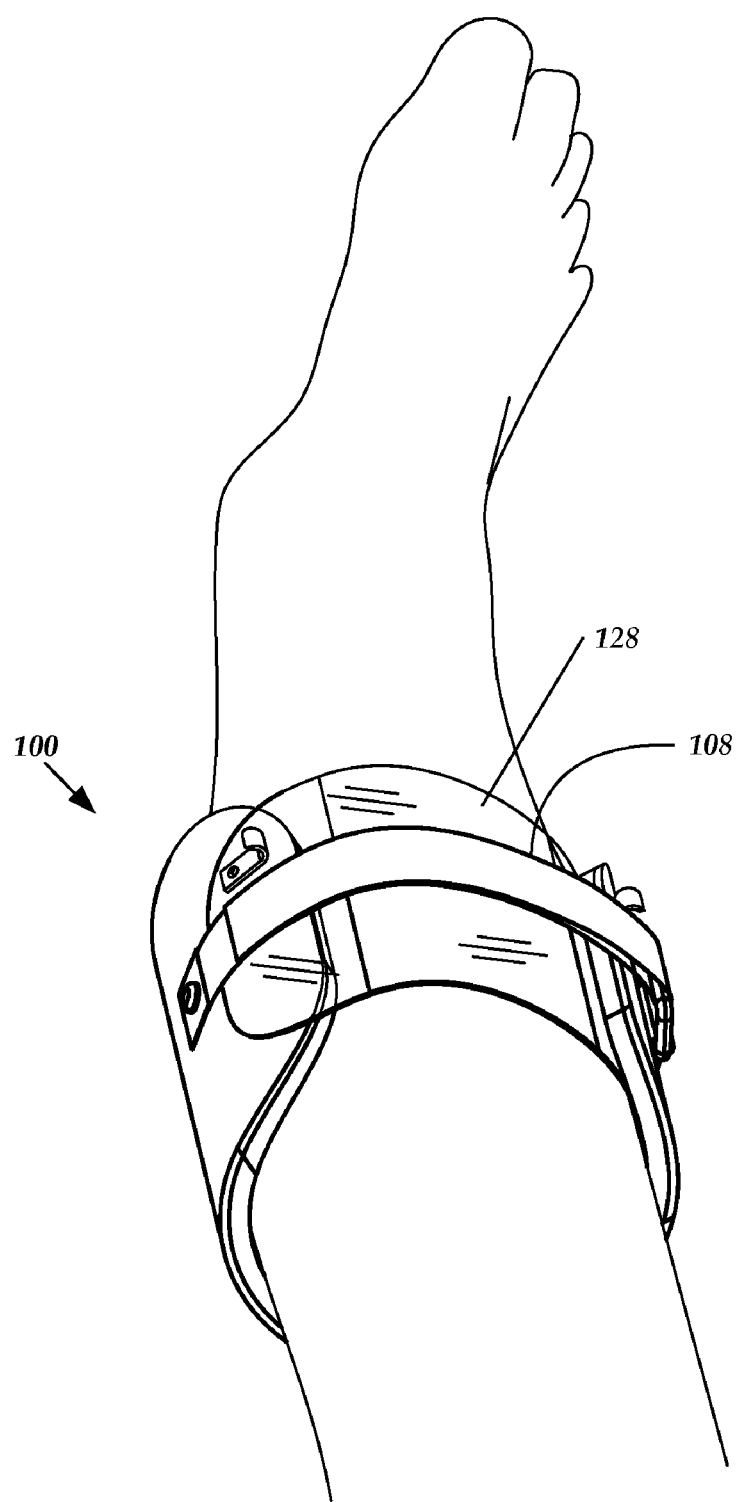
FIG. 6 depicts the apparatus of FIG. 1 releasably secured to the lower leg of the user.

FIG. 6 depicts the use of the elongate closure member 108 to releasably secure the apparatus 100 of FIG. 1 to the lower leg of the user. As shown in FIG. 6, the tongue member 128 shields and protects the user's leg from impingement or other discomfort as applied by the elongate closure member 108. In an alternative embodiment, the tongue member 128 can be replaced with a lining or other protecting material.

Figure 7:
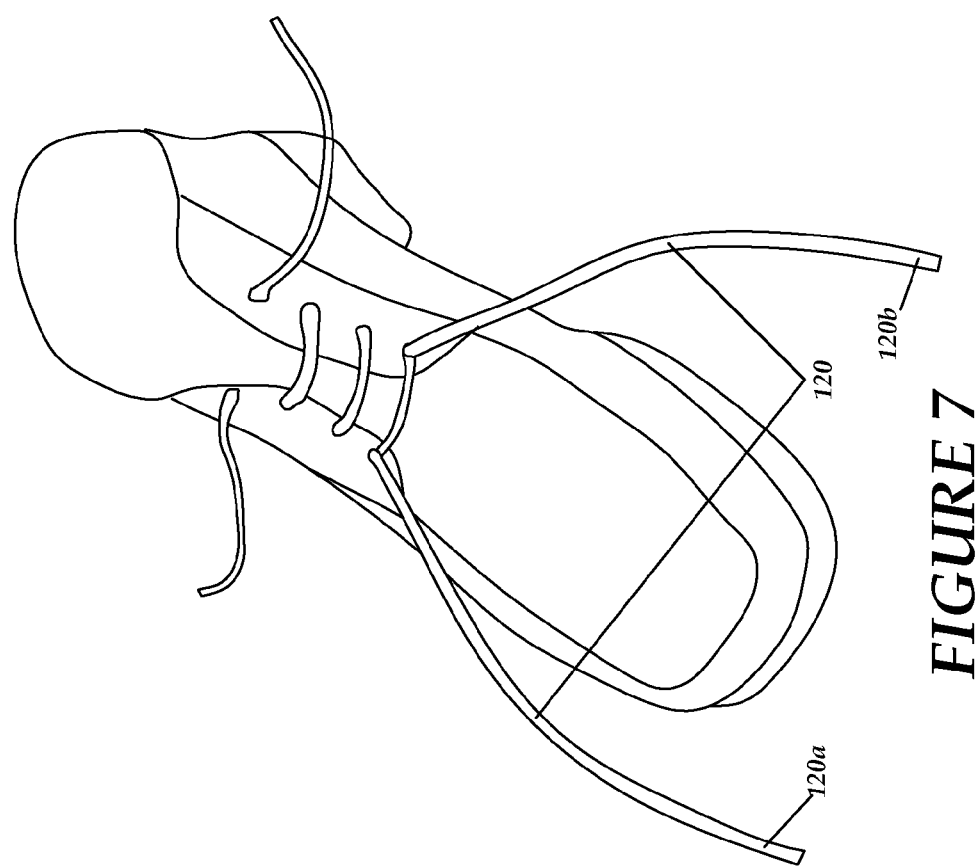
FIG. 7 depicts footwear of a user with a foot drop condition including an attachment means that can be used to orient the user's foot under an embodiment.

FIG. 7 depicts footwear of a user with a foot drop condition including an attachment means 120 to orient the user's foot under an embodiment. As shown, ends 120*a* and 120*b* of the attachment means 120 have been threaded through lacing retainers of the footwear.

Figure 8:
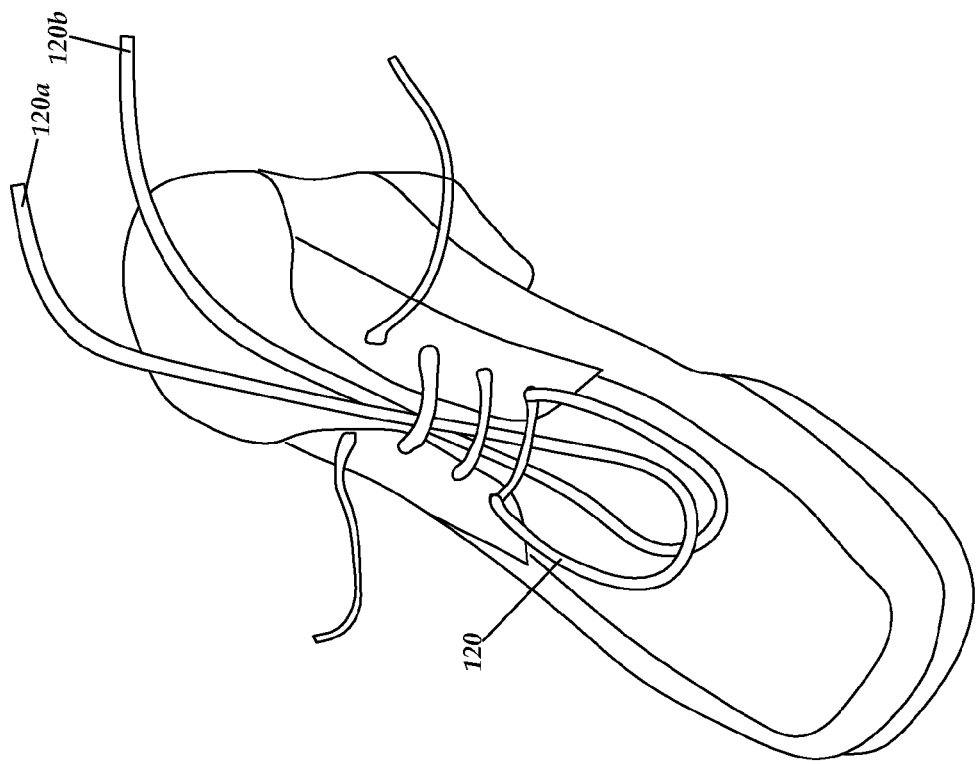
FIG. 8 depicts the footwear of FIG. 7 in preparing to use the attachment means to orient the user's foot.

FIG. 8 depicts the footwear of FIG. 7 in preparing to use the attachment means 120 (e.g., a durable shoe lace) to orient the user's foot. As shown in FIG. 8, the ends 120*a* and 120*b* of the attachment means 120 have been threaded below the existing laces of the footwear to exit at the top of the footwear near the user's ankle. Once the attachment means 120 has been secured to the lower leg member 102, the lifting force can be distributed over the dorsal portion of the affected foot since the attachment means 120 has been threaded below the existing laces as shown in FIG. 8. Accordingly, the distributed force can be used to maintain the affected foot at a desired orientation to reduce the foot drop condition.

Figure 9:
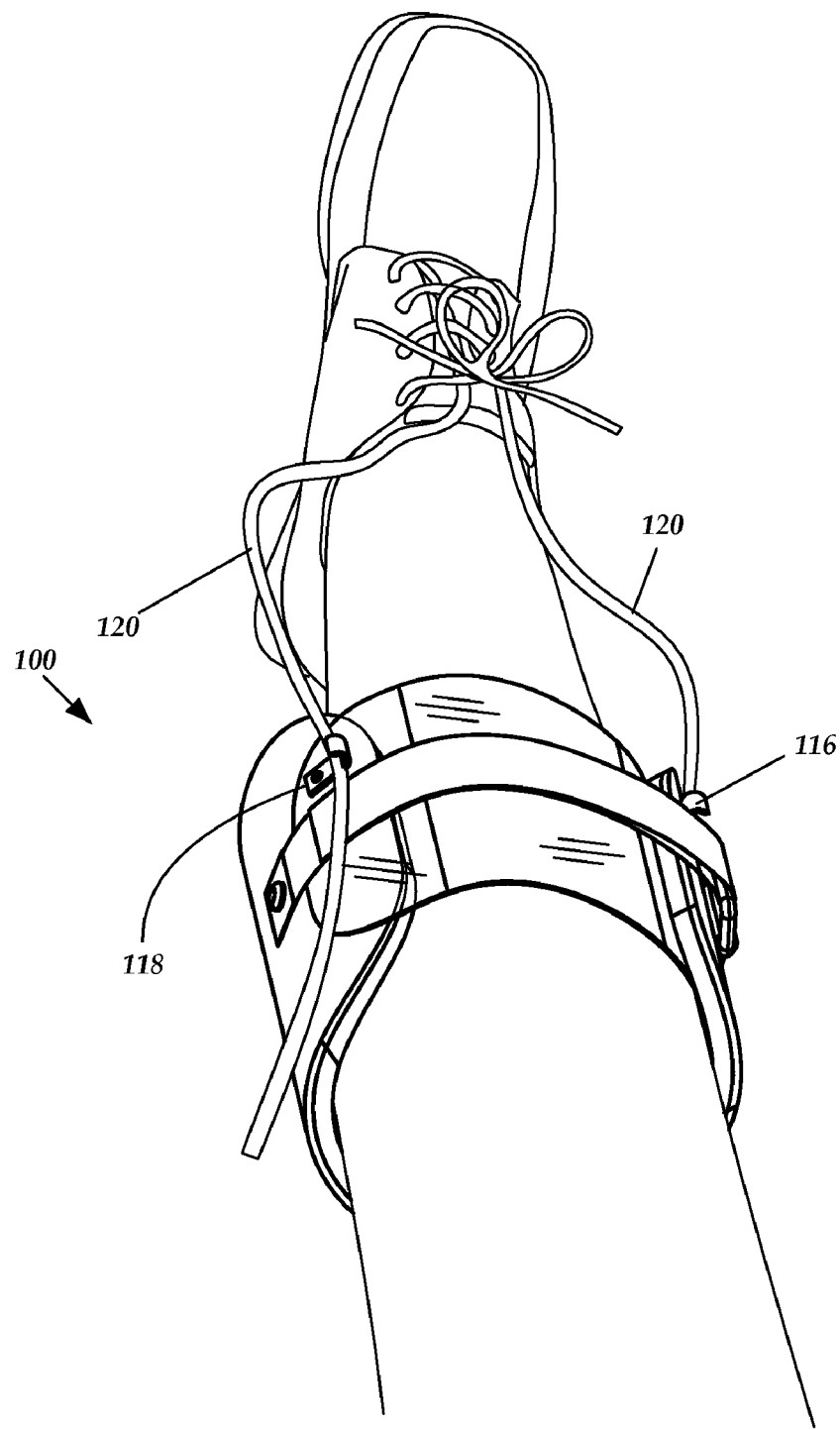
FIG. 9 depicts a user with a foot drop condition after securing the apparatus of FIG. 1 and showing footwear which includes attachment means for orienting the user's foot.

FIG. 9 depicts a user with a foot drop condition after securing the apparatus 100 of FIG. 1 and showing the footwear of FIG. 8 which includes the attachment means 120 for use in orienting the user's foot to a desired orientation. As shown in FIG. 9, the attachment means 120 has been releasably coupled to the pair of attachment members 116 and 118 located in proximity to a frontal portion of the lower leg member 120 below the elongate closure member 108.

Figure 10:
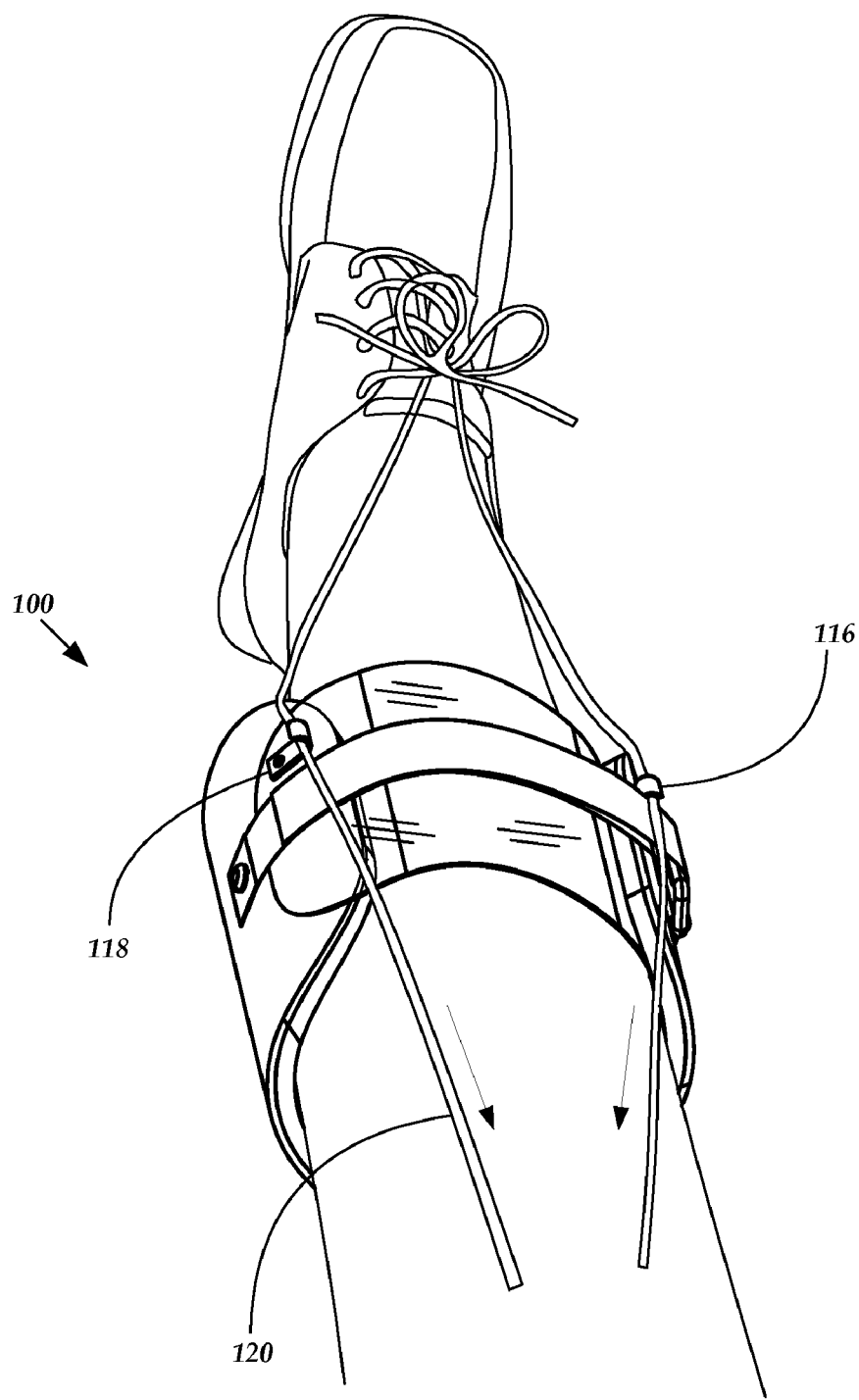
FIG. 10 depicts a user with a foot drop condition after securing the apparatus of FIG. 1 and showing footwear which includes attachment means for orienting the user's foot.

FIG. 10 depicts a user with a foot drop condition after securing the apparatus 100 of FIG. 1 and showing the footwear of FIG. 8 as the user pulls (shown by the two arrows) the attachment means 120 to orient the user's foot at a desired orientation and preparing to use the pair of attachment members 116 and 118 to support a force to maintain the foot at the desired orientation by securing the attachment means 120. FIG. 1 shows the apparatus 100 maintaining the user's foot at a desired orientation after securing the attachment means 120.

Figure 11:
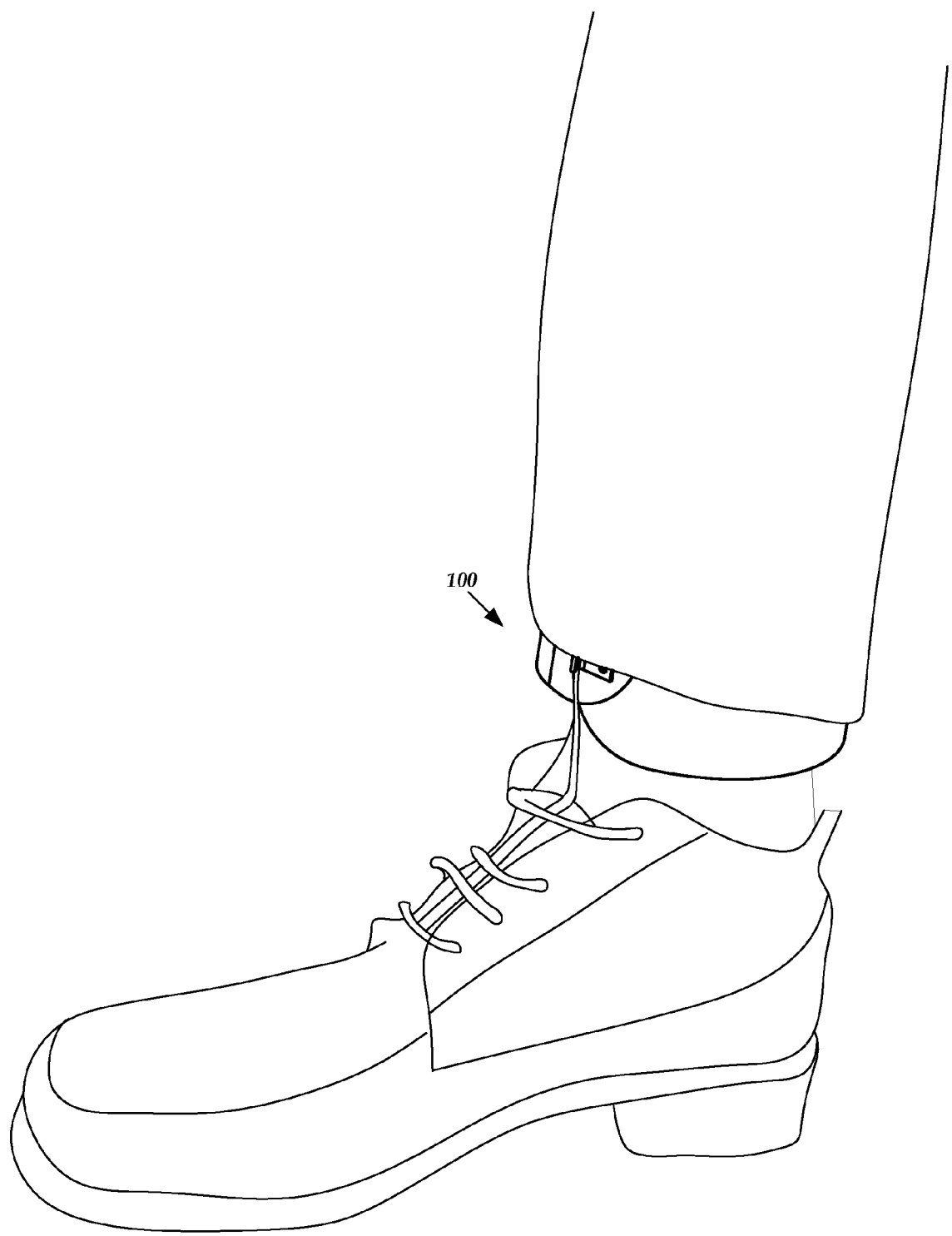
FIG. 11 depicts a user with a foot drop condition after securing the apparatus of FIG. 1 and using the attachment means to orient the user's foot.

FIG. 11 depicts a user with a foot drop condition after securing the apparatus 100 of FIG. 1 and after securing the attachment means 120 to orient the user's foot at the desired orientation. As shown in FIG. 11, the apparatus 100 can be worn discreetly by the user since the apparatus 100 is not required to be inserted inside of the user's footwear. Moreover, the apparatus 100 is designed to be lightweight and not bulky to provide a comfortable solution to reduce the foot drop condition.

In another embodiment, a slip-on component having eyelets or other attachment means can be included with the apparatus 100 and used with a user's footwear that may not include eyelets or other means for coupling the lower leg member 102 to the footwear. In yet another embodiment, a grommet making device or other tool can be used to form one or more eyelets on existing footwear that may not include eyelets and/or shoelaces. The tool can be used to form one or more eyelets towards a toe portion of the footwear and a lace or similar coupling member can be used to couple the footwear to the lower leg member 102 using the attachment members 116 and 118. In this manner, a user can use existing footwear, such as dress shoes or boots that do not have eyelets.

FIG. 12 is a right side view of an apparatus 200 that can be used to reduce a foot drop condition under an embodiment.

FIG. 13 is a left side view of the apparatus 200 of FIG. 12.

Figure 14:
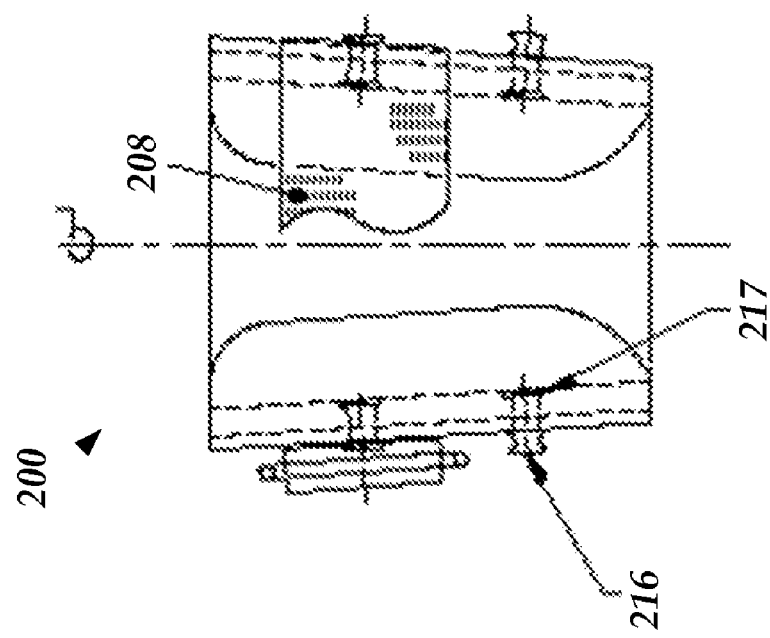
FIG. 14 is a front view of the apparatus of FIG. 12.

FIG. 14 is a front view of the apparatus 200 of FIG. 12.

Figure 15:
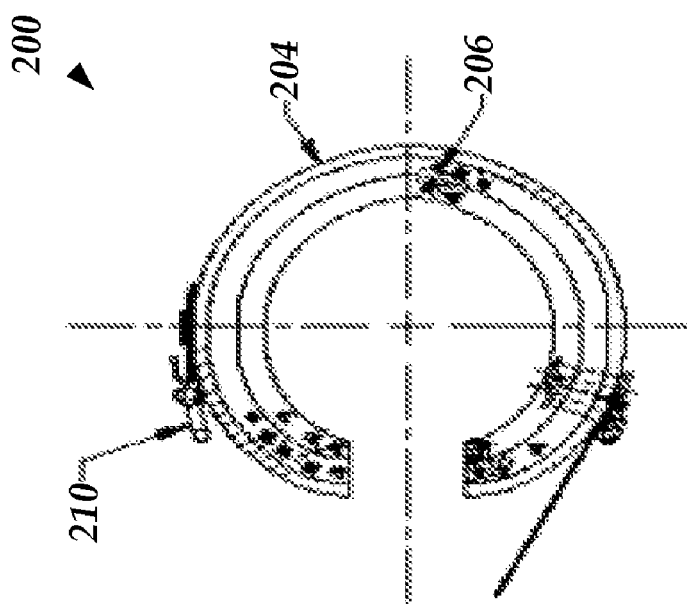
FIG. 15 is a top view of the apparatus of FIG. 12.

FIG. 15 is a top view of the apparatus 200 of FIG. 12.

As shown in FIGS. 12-15, the apparatus 200 can be configured to be used to reduce a foot drop condition. The apparatus 200 can be used by a user to improve mobility issues and conditions, including issues associated with walking, standing, running, etc. For example, the apparatus 200 can be used by a user to reduce the likelihood of tripping due to an unintentional drop of the foot. The apparatus 200 can be readily manufactured and tailored to a size and a dimension that conforms to a size and dimension of a specific user's lower leg as measured above the ankle and below the calf. The apparatus 200 can be adjusted to a desired orientation according to a user's preference.

The apparatus 200 includes a molded lower leg member 202. The lower leg member 202 includes an inner layer 204 and an outer layer 206. The inner layer 204, or a portion thereof, can be manufactured using a cushioning material to provide a better seal (e.g. more surface to surface friction) when the lower leg member 202 is attached to a user's lower leg. The inner material can be made to be breathable and light to provide a comfortable buffer to the outer layer. For example, the lower leg member 202 can be molded using a vacuum molding process to have a height of about 2 inches to about 6 inches, wherein the inner layer 204 can comprises a foam material and includes a thickness of about 0.125 inches to about 0.50 and the outer layer 206 can comprise a plastic material and includes a thickness of about 0.0625 inches to about 0.25 inches.

In an embodiment, the inner layer 204 comprises a cushioning material, such as a heat moldable foam material for example, and the outer layer 206 comprises a rigid but flexible material, such as a thermoplastic, plastic, or other material for example. As shown in FIGS. 14 and 15, the lower leg member 202 can be molded into a frustoconical or cylindrical shape having a substantially C-shaped cross-section that conforms to a size and dimension of a user's lower leg who is afflicted with a foot drop condition. However, the size, dimension, configuration, and materials of the lower leg member 202 can be configured to conform to a particular user and any associated requirements.

The apparatus 200 also includes an elongate strap 208 that can be attached to the lower leg member 202 and used to secure the lower leg member 202 to user's leg above the ankle and below the calf muscle. In one embodiment, the elongate strap 208 comprises a strap having a length and a width (e.g., a width of about 0.50 inches to about 2 inches and a length of about 8 inches to about 15 inches) that includes a first hook portion 208a and a second loop portion 208b. The elongate strap 208 can be pulled tight and the first hook portion 208a can be attached to the second loop portion 208b to releasably secure the lower leg member 202 to the user's lower leg. In another embodiment, the elongate strap 208 comprises an adjustable strap that includes male and female buckling members, snaps, or other fasteners that can be used to secure the lower leg member 202 to the user's lower leg.

As shown in FIG. 12, a first end of the elongate strap 208 can be securely attached to a side portion of the lower leg member 202 and a second end can be used to releasably secure the lower leg member 202 to the user's lower leg. For example, a rivet, screw, or other fastening device 209 can be used to secure the first end of the elongate strap 208 to the lower leg member 202 and the second end can be releasably attached to another portion of the elongate strap 208 or the lower leg member 202.

The elongate strap 208 can be threaded through a threading member 210 and adjustably secured to compress and secure the lower leg member 202 to the user's lower leg. The threading member 210 can be used in conjunction with the elongate strap 208 to secure the lower leg member 202 to the user's lower leg. In one embodiment, the threading member 210 includes a chafe tab portion 212 and a loop, ring, or other threading portion 214 (e.g., D-loop, D-ring, tri-ring, etc.). The threading member 210 can be securely affixed to the lower leg member 202, such as by using a rivet, screw, or other fastener 215 for example.

The lower leg member 202 also includes a pair of attachment members 216 and 218 that can be used to couple the lower leg member 202 to a user's footwear, such as a shoe or a boot for example. An attachment means, such as a lace member of an elongate length of material that is used for tying or coupling for example, can be releasably and adjustably coupled to the lower leg member 202 using the pair of attachment members 216 and 218. For example, the pair of attachment members 216 and 218 can comprise a pair of metallic or plastic hooks, loops, rings, or other coupling structures that can be riveted or otherwise affixed using fasteners 217 to the lower leg member 202.

The pair of attachment members 216 and 218 can be located below the elongate strap 208 and affixed to a lower frontal portion of the lower leg member 202. In one embodiment, the pair of attachment members 216 and 218 can be located a distance of about one-quarter of the overall height (H) of the lower leg member 202 as measured from a lower edge and from a leading edge of the lower leg member 202.

Correspondingly, the amount and orientation of a force required to lift the affected foot can be optimized by locating the pair of attachment members 216 and 218 at the lower frontal portion (in front of the ankle bone towards the user's toes) of the lower leg member 202. For example, the amount of force required to lift and maintain the foot at the desired orientation can be focused on the dorsal portion of the foot by locating the pair of attachment members 216 and 218 at the lower frontal portion of the lower leg member and securing an attachment means (see FIG. 1) from the footwear to the pair of attachment members 216 and 218. Moreover, the length of the attachment means required to secure the foot can also be minimized by minimizing the distance between the pair of attachment members 216 and 218 and the user's footwear.

The apparatus 200 also includes a tongue member 220. The tongue member 220 can be coupled to the lower leg member 202, such as by using fastener 209 for example, and used to provide a shield to the elongate strap 208 and a secured attachment means coupled to a user's footwear. The tongue member 220 can be made of plastic or another lightweight material to prevent chafing or other discomfort that may be caused by the elongate strap 208 and/or a secured attachment means.

The apparatus 200 can be manufactured in various sizes for children and adults to substantially fit the circumference of a portion of the leg just above the ankle. The patient or individual can measure the circumference of the lower leg approximately 1 inch above the ankle bone in order to determine the correct size. According to one embodiment, the lower leg member 202 can be configured with a height of about 2 inches to about 6 inches having a substantially C-shaped cross section having approximately the same circumferential dimension throughout the height. The lower leg member 202 of various embodiments can be constructed using a sturdy, durable thermoplastic material, and includes some stretching flexibility to aide in attaching and removing and for the individual to comfortably wear on the lower portion of the leg just above the ankle. The lower leg member 202 can be made from other flexible, resilient, and/or sturdy materials.

In an embodiment, the lower leg member 202 can be manufactured by the use of a vacuum molding process. A mold, such as a plaster of paris mold, can be used in the molding process to manufacture the lower leg member 202. A number of pulling stations, such as 4 to 6 for example, can be attached to a vacuum pump. The pulling stations consist of a mold attached to a pipe that is fed thru to a tube leading to the pump to create a vacuum. In one embodiment, a first manufacturing step includes molding an inner layer of foam material or foam. The foam can be heated and wrapped around the mold. As the vacuum is created, the foam will form to the mold. The foam can be formed to a desirable width, such as about $\frac{1}{8}^{th}$ of inch to about $\frac{3}{8}^{th}$ of an inch for example. The second manufacturing step includes molding a plastic-type material. For example, a plastic-type material such as a co-polymer or other flexible material can be heated to about 400 degrees and applied to the foam, wrapping the material around the foam which has already formed around the mold.

As the vacuum is created which can include the assistance of a perforation tool being applied to the foam to create air flow, the plastic-type material will then form around the layer of foam that is formed around the mold. Additional layers of differing materials can also be included. The end result can be a 2 layer lower leg member 202 of materials formed to the mold. The foam and plastic are bonded together to form the sturdy and flexible lower leg member 202. After cooling, the materials can be removed from the mold by a saw or other cutting means, leaving a measured opening for attaching and removing the lower leg member 202 to and from the leg. The edges can be sanded and otherwise smoothed. The elongate strap 208 can be riveted or otherwise fastened to one side of the lower leg member 202 on a central to upper portion of the side. An anchor or threading member 210, such as a 1½" rectangular, triangular, or otherwise shaped chafe tab with a stainless steel loop for example, can be riveted or otherwise fastened to the opposing side of the lower leg member 202.

As described above, attachment members 216 and 218 (such as one, two, or three pairs of D-type hooks for example) can be riveted or otherwise fastened on each side of the lower leg member 202 below the strap 208 and threading member 210. For example, D-type hooks can be used for speed lacing the apparatus 200 once a lace member is tight enough to secure the foot in a desired position. A tongue or other padded material can be included (attached or separate). For example, a tongue made of padded material can be included with 2 slits for weaving the strap 208 through. The user can then slide the padded tongue to a desired position to provide cushioning between the skin and the laces. A durable lace member having two ends can be included with the apparatus 200. Moreover, another accessory to assist in tying shoes such as a cord-lock or other shoe tying devices that are used for children and other individuals can be included with the apparatus 200.

For example, a number of ovens or other heating means can be used when manufacturing the apparatus 200. A number of pipes attached to one or more motors or pumps (e.g., a 1-hp pump) can be used to provide pulling stations for manufacturing the apparatus 200. A plaster of paris, fiberglass, or other material can be used for a mold which can be attached to a pipe and the mold with a pipe slides into a larger diameter pipe associated with a pulling station. A hose attached to a pump can be used to feed each the pulling stations. Multiple hoses can feed multiple stations (e.g. each hose feeds 4 pulling stations). Each pulling station can include a shut off (to close the vacuum). The hoses create the vacuum that attaches to the mold. The vacuum can be used to draw the foam and hot plastic or other material to the associated mold. When a plaster of paris mold can no longer function, then more plaster of paris can be poured into a fiber glass mold to provide another molded plaster of paris mold with a pipe sticking out ready to insert into the larger diameter pipe of an associated pulling station.

While the embodiments describe various processing techniques, other techniques can be used to manufacture the apparatus 200. Additionally, other materials and combinations of different materials can be used to manufacture the apparatus 200.

Figure 16:
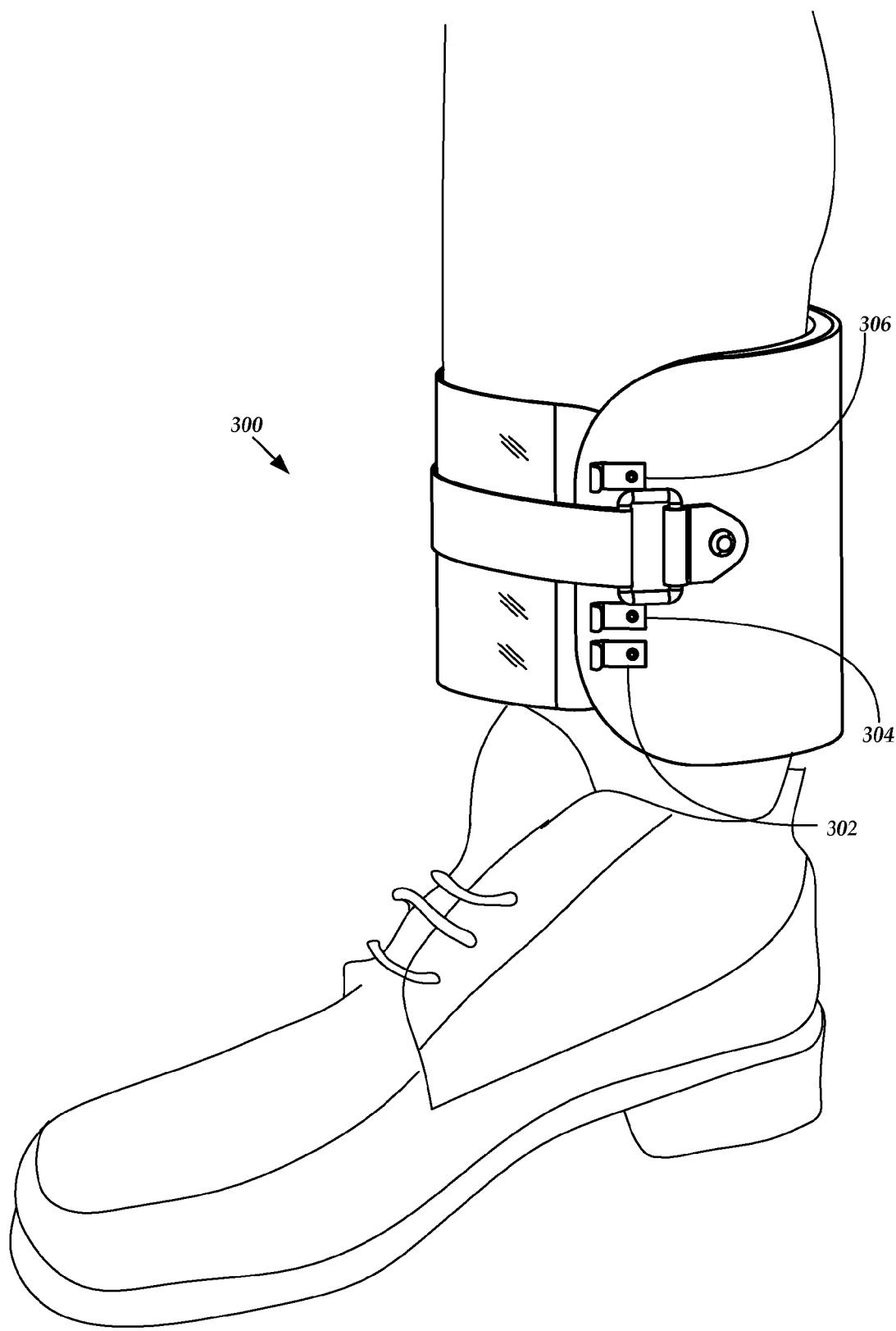
FIG. 16 depicts an apparatus having a plurality of hook members for use in orienting a user's foot under an embodiment.

FIG. 16 depicts an apparatus 300 having a plurality of hook members 302-306 for use in orienting a user's foot under an embodiment. Opposing hook members are disposed on an opposing side of the apparatus 300. One or more of the pairs of hook members can be used to attach an attachment means to secure and orient a user's foot at a desired orientation to reduce a foot drop condition. The extra hook members or other attachment members can be used to provide additional reinforcement when securing the foot at a desired orientation.

Figure 17:
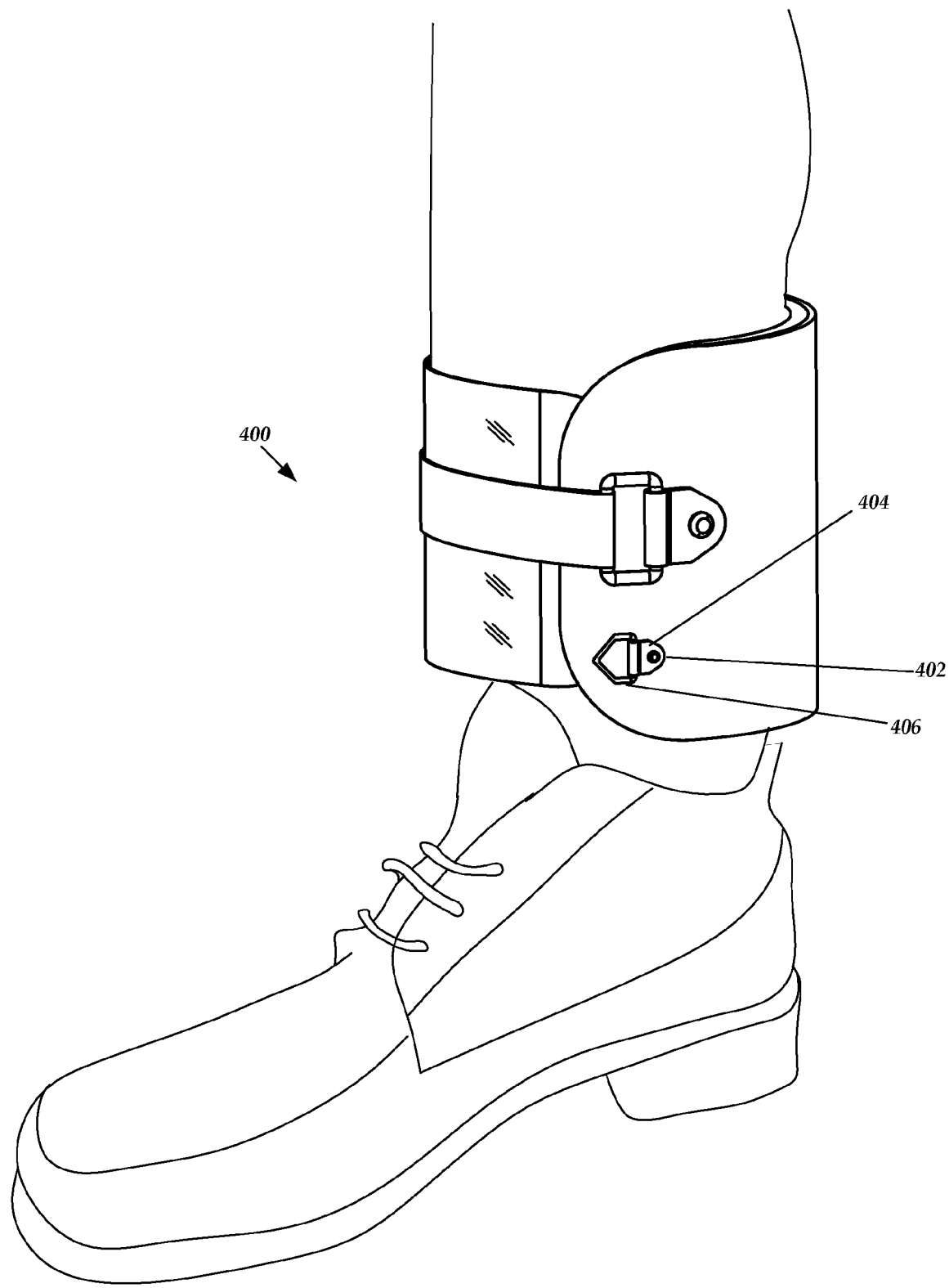
FIG. 17 depicts an apparatus having attachment members for use in orienting a user's foot under an embodiment.

FIG. 17 depicts an apparatus 400 having an attachment member 402 under an embodiment. An opposing attachment member is disposed on an opposing side of the apparatus 400. As shown in FIG. 17, the attachment member 402 includes a chafe tab portion 404 and a triangularly-shaped loop or ring portion 406. Other shapes can be used for the loop or ring portion 406. The attachment members can be used to attach an attachment means to secure and orient a user's foot at a desired orientation to reduce a foot drop condition.

According to the various embodiments users, including patients with handicaps, diabetes, stroke issues, etc. can continue to work and live almost normal lives by using an apparatus to reduce a foot drop condition. One of the drawbacks for patients and other users is the need to wear office attire while requiring a casual comfortable shoe. According to various embodiments, an apparatus to reduce a foot drop condition can be: configured in a variety of sizes to fit varying lower leg circumferences; configured in a variety of colors (black, skin tone, white, etc.) and various transfer patterns such as camouflage, sports, skateboarding, soccer, basketball, football, animals, butterflies, sailboats, rainbows, cartoon characters and others; worn discretely and made less obvious to others; configured to induce less pressure to skin beneficial to diabetes patients; configured to be used with more versatile, stylish footwear (including footwear having laces); configured so that footwear can be easily removed and replaced without embarrassment since the lower leg member can remain secured to the lower leg.

While certain configuration are described for various embodiments described above, other embodiments and configurations are available.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize.

The elements and acts of the various embodiments described above can be combined to provide further embodiments. These and other changes can be made to the invention in light of the above detailed description. Aspects of the invention can be modified, if necessary, to employ the systems, functions and concepts of the various patents and applications described above to provide yet further embodiments of the invention.

In general, in the following claims, the terms used should not be construed to limit the invention to the specific embodiments disclosed in the specification and the claims. Accordingly, the invention is not limited by the disclosure, but instead the scope of the invention is to be determined entirely by the claims.

While certain aspects of the invention are presented below in certain claim forms, the various aspects of the invention can be contemplated in any number of claim forms. Accordingly, additional claims can be added after filing the application to pursue such additional claim forms for other aspects of the invention.

What is claimed is:

1. An apparatus that can be used to reduce a foot drop condition, the apparatus comprising:
    a molded lower leg member having a height, an opening, and a C-shaped cross section throughout the height, wherein the lower leg member has a size and dimension to be coupled to a portion of a lower leg below a calf muscle and above a foot and encompass a substantial portion of the lower leg such that the opening of the lower leg member is disposed over a front portion of the lower leg when the lower leg member is coupled to the portion of the lower leg, the lower leg member having an inner layer of a first material and an outer layer of a second material, wherein the apparatus is not inserted in the user footwear when coupled to the portion of the lower leg;
    an elongate closure member disposed on the lower leg member and configured to releasably secure the lower leg member to the portion of the lower leg;
    a pair of attachment members disposed below the elongate closure member and located on opposing sides of the opening at lower frontal portions of the lower member, wherein the pair of attachment members releasably couple to a lacing member that is coupled to footwear on the foot and the pair of attachment members support a force required to lift and maintain the foot at a desired orientation when the lacing member is secured such that a lifting force is coupled to the pair of attachment members located at the lower frontal portions of the lower leg member and distributed over a dorsal portion of the foot when coupled to the portion of the lower leg; and,
    a shield attached to one of the opposing sides of the lower leg member and to at least be positioned between a secured lacing member and an exposed portion of the lower leg through the opening when the lower leg member is coupled to the portion of the lower leg.

2. The apparatus of claim 1, wherein the molded lower leg member comprises a substantially C-shaped cross-sectional configuration and includes similar cross-sectional dimensions throughout the height, wherein the first material of the inner layer includes heat moldable foam and the second material of the outer layer includes thermoplastic.

3. The apparatus of claim 2, wherein the molded lower leg member includes a height of about 2 inches to about 6 inches.

4. The apparatus of claim 1, wherein the inner layer has a thickness of about 0.125 inches to about 0.50 inches and the outer layer has a thickness of about 0.0625 inches to about 0.25 inches.

5. The apparatus of claim 4, wherein the outer layer comprises a plastic material and the inner layer comprises a foam material.

6. The apparatus of claim 4, wherein the inner and outer layers are formed using a mold and a vacuum.

7. The apparatus of claim 1, wherein the elongate closure member comprises a strap having a first hook portion and a second loop portion is threaded through an anchor and the first hook portion and second loop portion are attached together to secure the lower leg member to the portion of the lower leg.

8. The apparatus of claim 7, wherein the strap includes a first end attached to an outer side of the lower leg member and a second end to be threaded through a structure having an opening disposed on an opposing outer side of the lower leg member, wherein the shield protects the user skin from the strap when the apparatus is coupled to the portion of the lower leg.

9. The apparatus of claim 1, wherein the attachment members comprise hooks attached to a forward portion of the lower leg member to releasably secure the lacing member to the lower leg member to thereby provide and maintain a lift force with respect to the foot.

10. The apparatus of claim 1, wherein the attachment members comprise structures attached to a forward portion of the lower leg member, wherein each structure includes an enclosed opening for threading the lacing member to releasably secure to the lower leg member and thereby provide and maintain a lift force with respect to the foot.

11. The apparatus of claim 1, wherein the shield includes a lightweight plastic tongue member for covering the opening of the lower leg member and shielding the elongate closure member and an attached lace from the portion of the lower leg, the shield sized and dimensioned to prevent impingement caused by one of the lacing member and the elongate closure member.

12. An orthosis device that can be used to reduce a foot drop condition, the orthosis device comprising:

a molded flexible lower leg member having an opening and a substantially C-shaped cross section throughout the height, wherein the lower leg member has a size and dimension to be coupled to a portion of a lower leg below a calf muscle and above a foot and encompass a substantial portion of the lower leg such that the opening of the lower leg member is disposed over a front portion of the lower leg when the lower leg member is coupled to the portion of the lower leg, the lower leg member having an inner layer of a first material and an outer layer of a second material;

a securing means disposed on the lower leg member and configured to releasably secure the lower leg member to the portion of the lower leg;

a pair of attachment means disposed below the securing means and located on opposing sides of the opening at lower frontal portions of the lower leg member, wherein the pair of attachment means releasably couple to a lace that is coupled to footwear on the foot and the pair of attachment means support a force required to lift and maintain the foot at a desired orientation when the lace is secured such that a lifting force is coupled to the pair of attachment means located at the lower frontal portions of the lower leg member and distributed over a dorsal portion of the foot when coupled to the portion of the lower leg; and, shielding means attached to a side of the lower leg member and to at least be positioned between a secured lace and an exposed portion of the lower leg when the lower leg member is coupled to the portion of the lower leg, wherein the device is not inserted in the user footwear when coupled to the portion of the lower leg.

13. The orthosis device of claim 12, wherein the pair of attachment means are disposed on the lower frontal portions of the flexible lower leg member and support the lifting force to maintain a foot at a desired orientation, wherein the lower leg member includes similar cross-sectional dimensions throughout the height.

14. The orthosis device of claim 13, wherein the pair of attachment means comprise hook structures which are fixedly attached to the lower leg member.

15. The orthosis device of claim 13, wherein the pair of attachment means comprise tab and ring structures, wherein the tab and ring structures are fixedly attached to the flexible lower leg member.

16. The orthosis device of claim 12, wherein the flexible lower leg member can be molded using a vacuum and a mold being of a size and a dimension to conform to a lower leg portion above an ankle and below a calf muscle.

17. The orthosis device of claim 12, wherein the inner layer comprises a cushioning material of heat moldable foam and the outer layer comprises a rigid plastic material.

18. A method of reducing a foot drop condition, the method comprising:
coupling a molded lower leg member having a C-shaped cross section throughout the height to a lower leg portion below a calf muscle and above a foot to encompass the lower leg portion including a rear leg portion and side leg portions, wherein the molded lower leg member includes an opening for receiving the lower leg portion, an inner layer of a first material, and an outer layer of a second material formed using a vacuum molding process, wherein the opening of the lower leg member is disposed over a front leg portion when the lower leg member is coupled to the lower leg portion;

securing the molded lower leg member to the lower leg portion by threading an elongate closure member having a first hook portion and a second loop portion through an anchor and attaching the first hook portion to the second loop portion to secure the molded lower leg member to the lower leg portion;

disposing a shield attached to a side portion of the lower leg member to at least be positioned to encompass at least a portion of the opening of the lower leg member between a secured lacing member and an exposed portion of the lower leg when the lower leg member is coupled to the portion of the lower leg; and, orienting the foot with respect to the molded lower leg member by moving the foot upward to a desired orientation and securing a lace member attached to footwear using a pair of attachment members disposed below the elongate closure member at lower frontal portions of the lower leg member to support the force applied by the lace member to the footwear that is required to lift and maintain the foot such that a lifting force is coupled to the pair of attachment members located at the lower frontal portions of the lower leg member and distributed over a dorsal portion of the foot when coupled to the lower leg portion.

19. The method of claim 18, further comprising threading ends of the lace member through first and second lace retainers of the footwear before securing the lace member using a pair of hooks to support the force applied by the lace member to the footwear.

20. The method of claim 18, further comprising molding the molded lower leg member using a mold sized and dimensioned to a user and using a vacuum process to mold the inner and outer layers of the molded lower leg member.

* * * * *